United States Patent [19]
Chiaramonte et al.

[11] Patent Number: 4,737,105
[45] Date of Patent: Apr. 12, 1988

[54] PRECISION DENTAL PLATES

[76] Inventors: Vincent Chiaramonte, 75 Farmers Ave., Lindenhurst, N.Y. 11757; Richard Bernstein, 4 Dogwood Hill, Brookville, N.Y. 11545

[21] Appl. No.: 886,659

[22] Filed: Jul. 18, 1986

Related U.S. Application Data
[63] Continuation-in-part of Ser. No. 638,199, Aug. 3, 1984.

[51] Int. Cl.⁴ ............................................. A61C 13/22
[52] U.S. Cl. .................................................... 433/180
[58] Field of Search ............... 433/180, 181, 182, 183, 433/215, 219

[56] References Cited

U.S. PATENT DOCUMENTS
| | | | |
|---|---|---|---|
| 1,332,415 | 3/1920 | Sigel | 433/183 |
| 1,369,509 | 2/1921 | Weintraub | 433/180 |
| 1,376,644 | 5/1921 | Russell | 433/180 |

*Primary Examiner*—Robert Peshock
*Attorney, Agent, or Firm*—James P. Malone

[57] ABSTRACT

Apparatus and method of mounting at least one false tooth in a vacant space between two good teeth. First and second right angled plates pre-manufactured to be mounted in slots in the top and one upper sidewall of each good tooth facing the vacant space. The plates have indentations or extensions to receive a post for the replacement tooth, teeth or bridge.

6 Claims, 1 Drawing Sheet

PRECISION DENTAL PLATES

TECHNICAL FIELD

This application is a continuation-in-part of prior application, Ser. No. 638,199, filed Aug. 3, 1984, for PRECISION DENTAL PLATES.

This invention relates to dental plates andmore particularly to dental plates for mounting teeth between two good teeth.

BACKGROUND ART

This invention is an improvement over prior U.S. Pat. No. 4,445,862 of VINCENT CHIARAMONTE, which shows means formounting a post between two good teeth by cutting grooves in the two good teeth. The grooves require a rather deep cut in the teeth.

Prior application Ser. No. 638,199 requires flat plates and relatively deep cuts in the teeth, some of which are square and difficult to make.

THE INVENTION

This improvement eliminates the grooves and instead provides precision right angled plates mounted in the two good teeth. This improvement provides a more shallow cut in the teeth with more holding area and more strength for holding the teeth in place but the process is otherwise the same as described in previous U.S. Pat. No. 4,445,862.

OBJECTS OF THE INVENTION

The principal object of the invention is to provide new and improved means for mounting one or more teeth between two good teeth.

Another object of the invention is to provide new and improved means for mounting one or more teeth between two good teeth comprising first and second plates mounted in the two good teeth.

Another object of the invention is to provide new and improved means for mounting at least one false tooth in a vacant space between two good teeth comprising first and second right angled plates adapted to be mounted in slots in the top and one upper sidewall of each good tooth facing the vacant space.

These and other objects of the invention will be apparent from the following specifixcation and drawings of which FIG. 1 is a side view of an embodiment of the invention mounted on a tooth.

BEST MODE OF THE INVENTION

Figure 2:
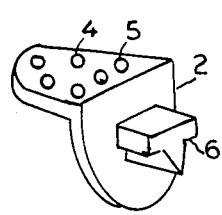
FIG. 2 is a perspective view of a plate with an extension member.
Figure 1:
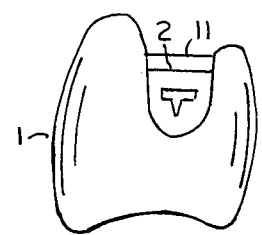

Referring to the Figures, FIGS. 1 and 2 show a tooth 1, having a plate 2, mounted thereon. In order to mount the plate, slots must be made in the sidewall and the top of the tooth so that the plate will fit in as shown in FIG. 1. Filling material 11 is placed on top.

The plate of FIG. 2 shows a plurality of holes 4, 5, etc., for applying cement to cement the plate to a tooth. FIG. 2 also shows a T shape extension member 6, which is adapted to fit into a corresponding indentation in the artificial tooth or bridge, which is to be attached.

Figure 3:
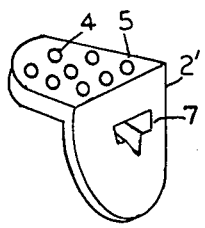
FIG. 3 is a perspective view of a plate with an indentation.

FIG. 3 shows a plate 2' having a T shaped indentation 7.

Figure 4:
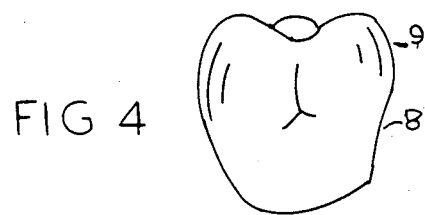
FIG. 4 is a front view of a tooth with a curved surface.

FIG. 4 shows a tooth 8 having a curved upper side surface 9.

Figure 5A:
FIG. 5A is a top view of FIG. 5.
Figure 5:
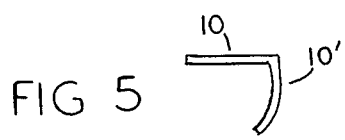
FIG. 5 is a side view of a plate for the tooth of FIG. 4.

FIG. 5 shows a plate 10, having a curved side surface 10' which is adapted to fit the curved surface of the tooth 8 after the tooth has been cut to receive the plate.

FIG. 5A shows a top view of FIG. 5 showing indentations 11, 12, etc., for cementing the plate to a slot cut in the top of the tooth.

In order to mount the plates, the tooth is first slotted in the shape of the plate, i.e., it is slotted at the top and on the upper side surface facing the vacant space where it is desired to insert a new tooth or teeth.

Figure 6:
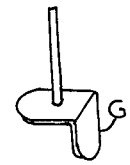
FIG. 6 is a pespective view of a slot gauge.

The slot that is cut does not have to be cut very accurately. The Dentist cuts the tooth to where he thinks will give proper support for the missing pontic. He then uses the gauge guide G, FIG. 6, that comes with a kit. The plates preferably come manufactured in different sizes along with a depth gauge for each corresponding size. He chooses the gauge that fits the closest to the slot he cut. He then select the corresponding plate which may have some play in the slot which poses little problem because the means of cementation is "bonding". This is where the natural tooth is acid etched, exposing tiny holes in the natural tooth enamel creating a mechanical "cement like" joining of the plate to the tooth. Standard cement is not as good as bonding. After He bonds the plates in place, He then takes an impression and sends it to the Lab to fabricate the bridge, for instance, per U.S. Pat. No. 4,445,862.

It is claimed:

1. Means for mounting at least one conventional false tooth in a vacant space between two good teeth comprising first and second right angled flat plates adapted to be mounted in slots in the top and one upper sidewall of each good tooth facing the vacant space, whereby a false tooth adapted to be connected onto the plates may be so mounted.

2. Apparatus as in claim 1 wherein atleast one plate has indentations.

3. Apparatus as in claim 1 wherein at least one plate has extensions.

4. Apparatus as in claim 1 wherein the plates are bonded to the good teeth.

5. Apparatus as in claim 1 wherein the plates are cemented to the good teeth.

6. Apparatus as in claim 1 wherein the upper side surface is curved and the side plate portions are correspondingly curved.

* * * * *